United States Patent
Wolf et al.

(10) Patent No.: US 8,660,663 B2
(45) Date of Patent: Feb. 25, 2014

(54) LEAD HAVING A CONDUCTIVE POLYMER CONDUCTOR

(75) Inventors: Peter J. Wolf, Dresser, WI (US); Jared Rud, Spring Lake Park, MN (US); Shrojalkumar Desai, Lake Bluff, IL (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 109 days.

(21) Appl. No.: 13/301,415

(22) Filed: Nov. 21, 2011

(65) Prior Publication Data

US 2012/0158107 A1    Jun. 21, 2012

Related U.S. Application Data

(60) Provisional application No. 61/425,005, filed on Dec. 20, 2010.

(51) Int. Cl.
*A61N 1/375*    (2006.01)

(52) U.S. Cl.
USPC .......................................................... 607/116

(58) Field of Classification Search
USPC .......................................................... 607/116
See application file for complete search history.

(56) References Cited

U.S. PATENT DOCUMENTS

| | | |
|---|---|---|
| 3,328,372 A | 6/1967 | Thomas et al. |
| 3,427,366 A | 2/1969 | Verdol et al. |
| 3,642,964 A | 2/1972 | Rausch et al. |
| 3,755,265 A | 8/1973 | Fletcher et al. |
| 4,043,331 A | 8/1977 | Martin et al. |
| 4,103,079 A | 7/1978 | Thaler |
| 4,276,394 A | 6/1981 | Kennedy et al. |
| 4,316,973 A | 2/1982 | Kennedy |
| 4,342,849 A | 8/1982 | Kennedy |
| 4,423,185 A | 12/1983 | Matsumoto et al. |
| 4,477,604 A | 10/1984 | Oechsle, III |
| 4,484,586 A | 11/1984 | McMickle et al. |
| 4,486,572 A | 12/1984 | Kennedy |
| 4,570,270 A | 2/1986 | Oechsle, III |
| 4,675,361 A | 6/1987 | Ward |
| 4,686,137 A | 8/1987 | Ward, Jr. et al. |
| 4,752,626 A | 6/1988 | Hoye et al. |
| 4,767,885 A | 8/1988 | Kennedy |
| 4,771,082 A | 9/1988 | Solodovnik et al. |
| 4,861,830 A | 8/1989 | Ward |
| 4,880,883 A | 11/1989 | Grasel et al. |
| 4,888,389 A | 12/1989 | Kennedy et al. |
| 4,906,673 A | 3/1990 | Mori |

(Continued)

FOREIGN PATENT DOCUMENTS

| | | |
|---|---|---|
| JP | 11131325 A | 5/1999 |
| WO | WO8704625 A1 | 8/1987 |

(Continued)

OTHER PUBLICATIONS

International Search Report and Written Opinion issued in PCT/US2011/061692, mailed Feb. 9, 2012, 9 pages.

(Continued)

*Primary Examiner* — Eric D. Bertram
(74) *Attorney, Agent, or Firm* — Faegre Baker Daniels LLP

(57) ABSTRACT

A medical electrical lead includes a conductive polymer conductor fabricated from a conductor-filled polyisobutylene urethane, urea or urethane/urea copolymer.

10 Claims, 5 Drawing Sheets

(56) References Cited

U.S. PATENT DOCUMENTS

| | | | |
|---|---|---|---|
| 4,910,321 | A | 3/1990 | Kennedy et al. |
| 4,939,184 | A | 7/1990 | Kennedy |
| 5,000,875 | A | 3/1991 | Kolouch |
| 5,017,664 | A | 5/1991 | Grasel et al. |
| 5,026,814 | A | 6/1991 | Re et al. |
| 5,029,585 | A | 7/1991 | Lieber et al. |
| 5,120,813 | A | 6/1992 | Ward |
| 5,149,739 | A | 9/1992 | Lee |
| 5,194,505 | A | 3/1993 | Brugel |
| 5,212,248 | A | 5/1993 | Knoll et al. |
| 5,332,791 | A | 7/1994 | Knoll et al. |
| 5,332,798 | A | 7/1994 | Ferreri et al. |
| 5,340,881 | A | 8/1994 | Kennedy et al. |
| 5,428,123 | A | 6/1995 | Ward et al. |
| 5,442,010 | A | 8/1995 | Hauenstein et al. |
| 5,442,015 | A | 8/1995 | Kennedy et al. |
| 5,589,563 | A | 12/1996 | Ward et al. |
| 5,637,647 | A | 6/1997 | Faust |
| 5,663,234 | A | 9/1997 | Kennedy et al. |
| 5,677,386 | A | 10/1997 | Faust |
| 5,741,331 | A | 4/1998 | Pinchuk |
| 5,852,118 | A | 12/1998 | Horrion et al. |
| 5,874,484 | A | 2/1999 | Dirckx et al. |
| 5,898,057 | A | 4/1999 | Chiang et al. |
| 6,005,051 | A | 12/1999 | Kennedy et al. |
| 6,010,715 | A | 1/2000 | Wick et al. |
| 6,072,003 | A | 6/2000 | Horrion et al. |
| 6,093,197 | A | 7/2000 | Bakula et al. |
| 6,200,589 | B1 | 3/2001 | Kennedy et al. |
| 6,228,945 | B1 | 5/2001 | Kennedy et al. |
| 6,365,674 | B1 | 4/2002 | Kaufhold et al. |
| 6,444,334 | B1 | 9/2002 | Doi et al. |
| 6,545,097 | B2 | 4/2003 | Pinchuk et al. |
| 6,555,619 | B1 | 4/2003 | Kennedy et al. |
| 6,600,956 | B2 | 7/2003 | Maschino et al. |
| 6,627,724 | B2 | 9/2003 | Meijs et al. |
| 6,827,881 | B2 | 12/2004 | Molnar et al. |
| 6,849,667 | B2 | 2/2005 | Haseyama et al. |
| 6,870,024 | B2 | 3/2005 | Haubennestel et al. |
| 7,065,411 | B2 | 6/2006 | Verness |
| 7,101,956 | B2 | 9/2006 | Benz et al. |
| 7,105,622 | B2 | 9/2006 | Kennedy et al. |
| 7,196,142 | B2 | 3/2007 | Kennedy et al. |
| 7,231,259 | B2 | 6/2007 | Jenney et al. |
| 7,280,875 | B1 | 10/2007 | Chitre et al. |
| 7,289,856 | B1 | 10/2007 | Karicherla |
| 7,292,890 | B2 | 11/2007 | Whitehurst et al. |
| 7,347,751 | B2 | 3/2008 | Sweeney et al. |
| 7,358,306 | B2 | 4/2008 | Turri et al. |
| 7,504,052 | B2 | 3/2009 | Ehbing et al. |
| 7,553,546 | B1 | 6/2009 | Tan |
| 7,617,004 | B2 | 11/2009 | Bartels et al. |
| 7,715,922 | B1 * | 5/2010 | Tan ................. 607/116 |
| 8,324,290 | B2 | 12/2012 | Desai et al. |
| 8,501,831 | B2 | 8/2013 | Desai et al. |
| 2003/0125499 | A1 | 7/2003 | Benz et al. |
| 2003/0204022 | A1 | 10/2003 | Kennedy et al. |
| 2004/0054210 | A1 | 3/2004 | Benz et al. |
| 2004/0186545 | A1 | 9/2004 | Rosero et al. |
| 2004/0198901 | A1 | 10/2004 | Graham et al. |
| 2005/0031874 | A1 | 2/2005 | Michal et al. |
| 2005/0060022 | A1 | 3/2005 | Felt et al. |
| 2005/0288476 | A1 | 12/2005 | Yilgor et al. |
| 2006/0047083 | A1 | 3/2006 | Yilgor et al. |
| 2006/0223946 | A1 | 10/2006 | Faust et al. |
| 2006/0264577 | A1 | 11/2006 | Faust et al. |
| 2007/0093604 | A1 | 4/2007 | Kennedy et al. |
| 2007/0203302 | A1 | 8/2007 | Kennedy et al. |
| 2007/0282411 | A1 | 12/2007 | Franz et al. |
| 2008/0167423 | A1 | 7/2008 | Richards et al. |
| 2009/0187162 | A1 | 7/2009 | Ohara et al. |
| 2009/0292094 | A1 | 11/2009 | Larichev et al. |
| 2009/0326077 | A1 | 12/2009 | Desai et al. |
| 2010/0023104 | A1 | 1/2010 | Desai et al. |
| 2010/0025703 | A1 | 2/2010 | Towns et al. |
| 2010/0055470 | A1 | 3/2010 | Klun et al. |
| 2010/0069578 | A1 | 3/2010 | Faust et al. |
| 2010/0075018 | A1 | 3/2010 | Desai et al. |
| 2010/0107967 | A1 | 5/2010 | Tanaka et al. |
| 2010/0179298 | A1 | 7/2010 | Faust et al. |
| 2010/0241208 | A1 | 9/2010 | Pinchuk |
| 2011/0054580 | A1 | 3/2011 | Desai et al. |
| 2011/0054581 | A1 * | 3/2011 | Desai et al. ................. 607/116 |
| 2012/0077934 | A1 | 3/2012 | Faust et al. |
| 2013/0079487 | A1 | 3/2013 | Faust et al. |

FOREIGN PATENT DOCUMENTS

| | | |
|---|---|---|
| WO | WO9322360 A1 | 11/1993 |
| WO | WO9526993 A1 | 10/1995 |
| WO | WO9700293 A1 | 1/1997 |
| WO | WO9747664 A1 | 12/1997 |
| WO | WO9833832 A1 | 8/1998 |
| WO | WO9834678 A1 | 8/1998 |
| WO | WO03042273 A1 | 5/2003 |
| WO | WO2004014453 A1 | 2/2004 |
| WO | WO2004044012 A1 | 5/2004 |
| WO | WO2004113400 A2 | 12/2004 |
| WO | WO2006011647 A1 | 10/2006 |
| WO | WO2007117566 A2 | 10/2007 |
| WO | WO2008060333 A1 | 5/2008 |
| WO | WO2008066914 A1 | 6/2008 |
| WO | WO2008112190 A1 | 9/2008 |
| WO | WO2008127730 A1 | 10/2008 |
| WO | WO2008156806 A1 | 12/2008 |
| WO | WO2009058397 A1 | 5/2009 |
| WO | WO2009158600 A1 | 12/2009 |
| WO | WO2009158609 A1 | 12/2009 |
| WO | WO2010039986 A1 | 4/2010 |
| WO | WO2010078552 A1 | 7/2010 |
| WO | WO2010081132 A1 | 7/2010 |
| WO | WO2010111280 A1 | 9/2010 |
| WO | WO2011022583 A1 | 2/2011 |
| WO | WO2011060161 A1 | 5/2011 |

OTHER PUBLICATIONS

Muller, J.P. et al., "Surface modification of polyurethanes by multicomponent polyaddition reaction", Journal of Materials Science Letters 17(2), 1998, pp. 115-118.

Non-Final Office Action issued in U.S. Appl. No. 11/400,059, mailed Apr. 11, 2011.

Non-Final Office Action issued in U.S. Appl. No. 12/492,483, mailed Nov. 21, 2011, 11 pages.

Non-Final Office Action, issued in U.S. Appl. No. 12/685,858, mailed Feb. 15, 2012, 18 pages.

Notice of Allowance issued in U.S. Appl. No. 12/492,483, mailed Jul. 13, 2012, 9 pages.

Office Action issued in U.S. Appl. No. 11/400,059, mailed Aug. 24, 2010.

Ojha et al., "Synthesis and Characterization of Thermoplastic Polyurethaneureas based on Polyisobutylene and Poly (tetramethylene oxide) Segments", J. Macromolecular Science, Part A, vol. 47(3), pp. 186-191, Mar. 2010.

Ojha, Umaprasana et al., "Syntheses and characterization of novel biostable polyisobutylene based thermoplastic polyurethanes", Polymer 50(2009), 3448-3457.

Ojha, Umaprasana et al., "Synthesis and Characterization of Endfunctionalized Polyisobutylenes for Sharpless-type Click Reactions", Polymer Preprints 2007, 48(2), 786.

Puskas, J.E. et al., "polyisobutylene-based biomaterials", Journal of Polymer Science Part A: Polymer Chemistry, vol. 42, Issue 13 (2004) pp. 3091-3109.

Rajkhowa, Ritimoni et al., "Efficient syntheses of hydroxyallyl end functional polyisobutylenes, a precursors to thermoplastic polyurethanes", Polymer Reprints (American Chemical Society, Division of Polymer Chemistry) 2007, 48 (2), 233-234.

Ranade, S. et al., "Physical characterization of controlled release of paclitaxel from the TAXUS™ Express2™ drug-eluting stent", Journal of Biomedical Materials Research Part A, 71A (2004) 625-634.

(56) References Cited

OTHER PUBLICATIONS

Ranade, S.V. et al., Styrenic Block copolymers for Biomaterial and Drug Delivery Applications, Acta Biomater. Jan. 2005; 1(1): 137-44.
Santos, R. et al., "New Telechelic Polymers and Sequential Copolymers by Polyfunctional Initiator-Transfer-Agents (Inifers)", Polymer Bulletin, 11:341-348 (1984).
Simmons, Anne. et al., "The effect of sterilisation on a poly(dimethylsiloxane)/poly(hexamethylene oxide) mixed macrodiol-based Polyurethane elastomer", Biomaterials 2006, 27, 4484-4497.
Speckhard, T.A. et al., "New generation polyurethanes", Polymer News 1984, 9(12), 354-358.
Speckhard, T.A. et al., "Properties of Polyisobutylene Polyurethane Block Copolymers: 2. Macroglycols produced by the 'inifer' technique", Polymer, vol. 26, No. 1, Jan. 1985, pp. 55-78.
Speckhard, T.A. et al., "Properties of Polyisobutylene Polyurethane Block Copolymers: 3. hard segments based on 4,4'-dicyclohexylmethane diisocyanate (H12MDI) and butane diol", Polymer, vol. 26, No. 1, Jan. 1985, pp. 70-78.
Speckhard, T.A. et al., "Properties of Polyisobutylene-Polyurethane Block Copolymers", Journal of Elastomers and Plastics, vol. 15 (Jul. 1983), pp. 183-192.
Speckhard, T.A. et al., "Properties of Polyisobutylene-Polyurethane Block Copolymers: I. Macroglycols from Ozonolysis of Isobutylene-Isoprene Copolymer", Polymer Engineering and Science, Apr. 1983, vol. 23. No. 6, pp. 337-349.
Speckhard, T.A. et al., "Ultimate Tensite Properties of Segmented Polyurethane Elastomers", Rubber Chem. Technol., 59, 405-431 (1986).
Tan, J. et al., "In Vivo Biostability Study of a New Lead Insulation Material," Cardiostim 2006, Europace Supplements, 8, 179PW/9 (2006).
Tonelli, C. et al., "New Fluoro-Modified Thermoplastic Polyurethanes" Journal of Applied Polymer Science, vol. 87, Issue 14 (2003) 2279-2294.
Tonelli, Claudio et al., "New Perfluoropolyether Soft Segment Containing Polyurethanes", Journal of Applied Polymer Science, vol. 57, pp. 1031-1042 (1995).
Virmani, R. et al. Circulation Feb. 17, 2004, 109)6) 701-5.
Wang, F. Polydimethylsiloxane Modification of Segmented Thermoplastic Polyurethanes and Polyureas, PhD. Dissertation, Virginia Polytechnic Institute and State university, Apr. 13, 1998.
Weisberg, David M. et al., "Synthesis and Characterization of Amphiphilic Poly(urethaneurea)-comb-polyisobutylene Copolymers", Macromolecules 2000, 33(12), pp. 4380-4389.
Weissmuller, M. et al., "Preparation and end-linking of hydroxyl-terminated polystyrene star macromolecules", Macromolecular Chemistry and Physics 200(3), 1999, 541-551.
Wiggins, Michael J. et al., "Effect of soft-segment chemistry on polyurethane biostability during in vitro fatigue loading", Journal of biomedical materials research, 68(4), 2004, 668-683.
Wohlfarth, C., "Permittivity (Dielectric Constant) of Liquids", CRC Handbook, 91st ed. 2010-2011, p. 6-186 to 6-207.
Wright, James I., "Using Polyurethanes in Medical Applications", 5 pages. Downloaded from http://www.cmdm.com on Oct. 17, 2006.
Wu, Yuguang et al., "The role of adsorbed fibrinogen in platelet adhesion to polyurethane surfaces: A comparison of surface hydrophobicity, protein adsorption, monoclonal antibody binding, and platelet adhesion", Journal of Biomedical Materials Research, Part A, Sep. 15, 2005, vol. 74A, No. 4, pp. 722-738.
Xu, Ruijian et al., "Low permeability biomedical polyurethane nanocomposites", Journal of Miomedical Materials Resarch, 2003, vol. 64A, pp. 114-119.
Yang, M. et al., J. biomed. Mater. Res. 48 (1999) 13-23.
Yeh, J. et al., "Moisture diffusivity of Biomer® versus Biomer®-coated Polyisobutylene polyurethane urea (PIB-PUU): a potential blood sac material for the artificial heart", Journal of Materials Science Letters 13(19), 1994, pp. 1390-1391.
Yoon, Sung C. et al., "Surface and bulk structure of segmented poly(ether urethanes) with Periluoro Chain Extenders. 5. Incorporation of Poly(dimethylsiloxane) and Polyisobutylene Macroglycols", Macromolecules Mar. 14, 1994, 27(6), pp. 1548-1554.
Ako, Masayuke et al., "Polyisobutylene-based urethane foams I. Comparative reactivities of hydroxyl-terminated polyisobutylenediols and -triols and other hydroxyl-capped polyols with isocyanate", Polymer Bulletin 19(2), 137-143 (1988).
Ako, Masayuke et al., "Polyisobutylene-based urethane foams II. Synthesis and properties of novel polyisobutylene-based flexible polyurethane foams", Journal of Applied Polymer Science, vol. 37(5), Feb. 5, 1989, pp. 1351-1361.
Bela et al., Living Carbocation Polymerization. XX. Synthesis of Allyl-Telechelic Polyisobutylenes by One-Pot Polymerization-Functionalization polymer. Mater. Sci. Eng. 1988; 58:869-872.
Chang, Victor S.C. et al. "Gas Permeability, Water Absorption, Hydrolytic Stability and Air-Oven Aging of Polyisobutylene-Based Polyurethane Networks", Polymer Bulletin 8(2-3-4), 69-74 (1982).
Chen, Chi-Chang et al., "Solid Polymer Electrolytes III Preparation, Characterization, and Ionic Conductivity of New Gelled Polymer Electrolytes Based on Segmented, Perfluoropolyether-Modified Polyurethane", Journal of Polymer Science: Part A: Polymer Chemistry, vol. 40, pp. 486-495 (2002).
Cozzens, David et al., "Long term in vitro biostability of segmented polyisobutylene-based thermoplastic polyurethanes", Journal of Biomedicals Materials Research Journal, 2010, pp. 1-9.
De, Priyadarsi et al., "Carbocationic Polymerization of Isobutylene Using Methylaluminum Bromide Coinitiators: Synthesis of Bromoally Functional Polyisobutylene" Macromolecules, Oct. 2006, 39(2), 7527-7533.
De, Priyadarsi et al., "Relative Reactivity of C4 Olefins toward the Polyisobutylene Cation" Macromolecules 2006, 39, 6861-6870.
Erdodi, G., et al., "Polyisobutylene-Based Polyurethanes. III. Polyurethanes Containing PIB/PTMO Soft Co-Segments," J. Polym. Sci., Part A: Polym. Chem, 47:5278-5290 (2009).
Erdodi, G., et al., "Polyisobutylene-Based Polyurethanes. VI. Unprecedented Combination of Mechanical Properties and Oxidative/Hydrolytic Stability by H-Bond Acceptor Chain Extenders" J. Polym. Sci., Part A: Polym. Chem, 48:2361-2371 (2010).
Faust, R. et al., "Method to Prepare Block Copolymers by the Combination of Cationic and Anionic Polymerization", U.S. Appl. No. 12/225,905, filed Apr. 5, 2007.
Gadkari A. et al., "Preparation and biocompatibility of Novel Polar-Nonpolar Networks. Osynthesis, Characterization and Histological-Bacterial Analysis of Mixed Polytetrahydrofuran-Polyisobutylene Networks", Polymer Bulletin, vol. 22, No. 1, Jul. 1, 1989, pp. 25-32.
Giusti, Paolo et al., "Synthesis and Characterization of New potentially Hemocompatible Thermoplastic Elastomers", p. 371, Abstract.
Gunatillake, P.A. et al., "Poly(dimethylsiloxane)/Poly(hexamethylene oxide) Mixed Macrodiol Based Polyurethane Elastomers. I. Synthesis and Properties", Journal of Appl. Polym. Sci. 2000, 76, 2026-2040, © 2000.
Higashihara, T. et al., "Synthesis of Poly(isobutylene-block-methyl methacrylate) by a Novel Coupling Approach", Macromolecules, 39:5275-5279 (2006).
International Search Report and Written Opinion issued in PCT/US2006/013308, dated Aug. 25, 2006.
International Search Report and Written Opinion issued in PCT/US2007/008528, dated Oct. 2, 2007.
International Search Report and Written Opinion issued in PCT/US2007/012948, dated Nov. 28, 2007.
International Search Report and Written Opinion issued in PCT/US2010/028334, Dated May 6, 2010, 12 pages.
International Search Report and Written Opinion issued in PCT/US2010/047633, Dated Jun. 17, 2011, 12 pages.
International Search Report and Written Opinion issued in PCT/US2010/047633, Jun. 17, 2011, 12 pages.
International Search Report and Written Opinion issued in PCT/US2010/047703, Dated Jun. 17, 2011, 12 pages.
International Search Report and Written Opinion issued in PCT/US2010/047703, mailed Jun. 17, 2011, 12 pages.
International Search Report issued in PCT/US2009/048827, mailed Oct. 6, 2009, 3 pages.
International Search Report issued in PCT/US2009/048845, mailed Oct. 6, 2009, 3 pages.

(56) References Cited

OTHER PUBLICATIONS

International Search Report issued in PCT/US2010/020733, mailed May 6, 2010.

Ioffe, David et al., "Bromine, Organic Compounds", Kirk-Othmer Encyclopedia of Chemical Technology, vol. 4, pp. 340-365, © 2002.

Ivan, B. et al., "Synthesis of New Polyisobutylene-Based Polyurethanes", Am. Chem. Soc., Div. Org. Coat. Plast. Prepr., 43, 908-913 (1980).

Jenny, C. et al., "A New Insulation Material for Cardiac Leads with Potential for Improved performance", HRS 2005, HeartRhythm, 2, S318-S319 (2005).

Jewrajka, Suresh K. et al., "Polyisobutylene-Based Polyurethanes. II. Polyureas Containing Mixed PIB/PTMO Soft Segments", Journal of Polymer Science: Part A: Polymer Chemistry, vol. 47, 2787-2797 (2009).

Jewrajka, Suresh K. et al., "Polyisobutylene-Based Segmented Polyureas. I. Synthesis of Hydrolytically and Oxidatively Stable Polyureas", Journal of Polymer Science: Part A: Polymer Chemistry, vol. 47, 38-48 (2009).

Kang, Jungmee et al, "PIB-Based Polyurethanes. IV. The Morphology of Polyurethanes Containing Soft Co-Segments", Journal of Polymer Science Part A: Polymer Chemistry, vol. 47, 6180-6190 (2009).

Kang, Jungmee et al., "Rendering Polyureas Melt Processable", Journal of Polymer Science Part A: Polymer Chemistry, vol. 49, 2461-2467 (2011).

Kang, Jungmee et al., Polyisobutylene-Based Polyurethanes. V. Oxidative-Hydrolytic Stability and Biocampatibility, Journal of Polymer Science: Part A: Polymer Chemistry, vol. 48, 2194-2203 (2010).

Kennedy, J.P. et al., "Designed Polymers by Carbocationic Macromolecular Engineering: Theory and practice", Hanser Publishers 1991, pp. 191-193 and 226-233.

Kennedy, J.P. et al., "Polyisobutylene-Based Diols and Polyurethanes", Urethane Chemistry and Applications, Ed., K. H. Edwards, ACS Symp. Book Series, 172, Washington, D.C. 1981, pp. 383-391.

Kennedy, J.P. et al., "Polyisobutylene-Based Diols and Polyurethanes" Advances in Urethane Science and Technology, vol. 8, 1981, pp. 245-251.

Kennedy, J.P. et al., "Polyisobutylene-based Model urethane Networks, I. Initial characterization and Physical properties", Polymeric Materials Science and Engineering, vol. 49, Copyright 1983 by ACS, pp. 69-77.

Kennedy, Joseph P. Synthesis, Characterization and Properties of Novel Polyisobutylene-Based urethane Model Networks, Journal of Applied Polymer Science, vol. 33(7), May 20, 1987, pp. 2449-2465.

Kennedy, Joseph P. "Synthesis, Characterization and Properties of Polyisobutylene-Based Polyurethanes", 6th International Technical/Marketing Conference: Polyurethane-New Paths to Progress-Marketing—Technology, Journal of Cellular Plastics, 1983, 19:288-307.

Kennedy, Joseph P. "Synthesis, Characterization and Properties of Polyisobutylene-Based Polyurethanes", Journal of Elastomers and Plastics, vol. 17 (Jan. 1985), pp. 82-88.

Kennedy, Joseph P. "Synthesis, Characterization and Properties of Polyisobutylene-Based Polyurethanes", The Society of the Plastics Industry, Inc., polyurethane Division, Proceedings of the SPI—6th International Technical/Marketing Conference, Nov. 2-4, 1983, San Diego, CA, pp. 514-516.

Kennedy, Joseph P., "Polyurethanes Based on Polyisobutylenes", Chemtech, Nov. 1986, 16(11), pp. 694-697.

Lelah, M.D. et al., "Polyurethanes in Medicine", CRC Press, Boca Raton, FL 1986, Chapter 3.

Li, J. et al., "Polyisobutylene supports—a non-polar hydrocarbon analog of PEG supports", Tetrahedron, 61 (51):12081-12092, Dec. 2005.

Macias, A. et al., "Preparacion y reticulacion de poliisobutilenos de bajo peso molecular con grupos terminales reactivos", Revista de Plasticos Modernos, Num 332 (Abril '83), pp. 412-418.

Miller, J. A., "New Directions in Polyurethane Research", Organic Coatings and Applied Polymer Science Proceedings, vol. 47, Copyright 1982 by ACS, pp. 124-129.

Mitzner, E. et al., "Modification of poly(ether urethane) elastomers by incorporation of poly(isobutylene) glycol. Relation between polymer properties and thrombogenicity", J. Biomater. Sci. Polymer edn. vol. 7, No. 12, pp. 1105-1118 (1996).

Mitzner, E., "Modification of segmented poly(ether urethanes) by incorporation of Poly(isobutylene)glycol", J.M.S.—Pure Appl. Chem., A34(1), pp. 165-178 (1997).

Miyabayashi, Toshio et al., "Characterization of Polyisobutylene-Based Model Urethane Networks", Journal of Applied Polymer Science, vol. 31, pp. 2523-2532 (1986).

\* cited by examiner

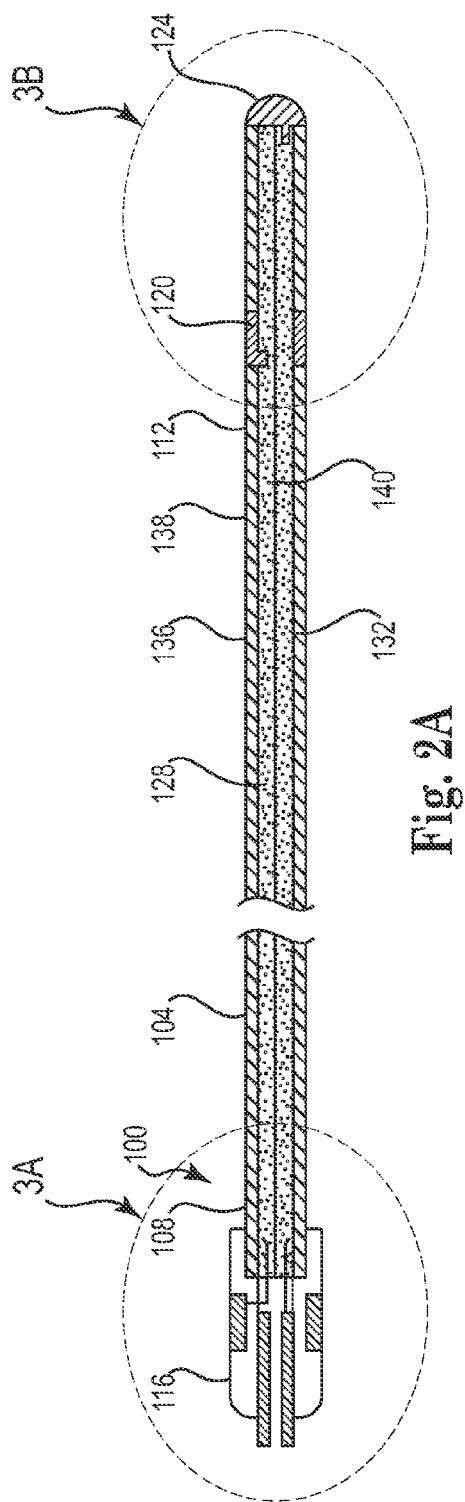
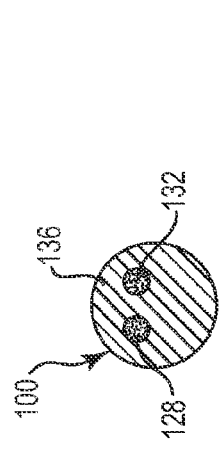
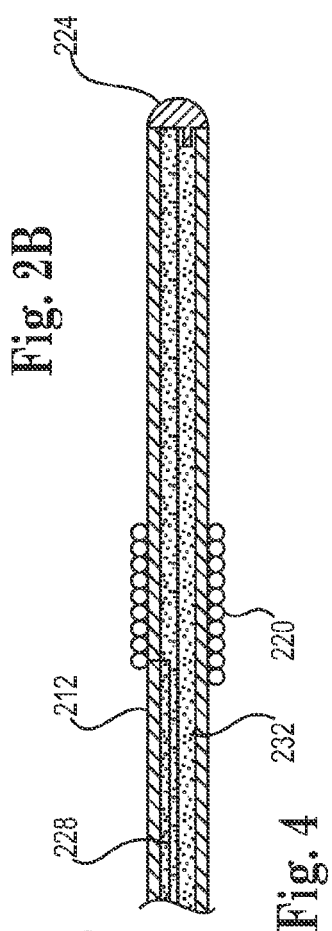

300

```
┌─────────────────────────────────────────────────┐
│ BLEND A PLURALITY OF CONDUCTIVE PARTICLES WITH A│
│ POLYISOBUTYLENE URETHANE, UREA OR URETHANE/UREA │—310
│ COPOLYMER TO FORM A CONDUCTIVE POLYISOBUTYLENE  │
│    URETHANE, UREA OR URETHANE/UREA COPOLYMER.   │
└─────────────────────────────────────────────────┘
                         │
                         ▼
┌─────────────────────────────────────────────────┐
│ EXTRUDE THE CONDUCTIVE POLYISOBUTYLENE URETHANE,│
│  UREA OR URETHANE/UREA COPOLYMER TO FORM AN     │—320
│       ELONGATE CONDUCTIVE POLYMER CONDUCTOR.    │
└─────────────────────────────────────────────────┘
                         │
                         ▼
┌─────────────────────────────────────────────────┐
│       FORM AT LEAST ONE LAYER OF AN INSULATING  │
│   POLYMERIC MATERIAL OVER THE ELONGATE CONDUCTIVE│—330
│                POLYMER CONDUCTOR.               │
└─────────────────────────────────────────────────┘
```

Fig. 5

LEAD HAVING A CONDUCTIVE POLYMER CONDUCTOR

CROSS-REFERENCE TO RELATED APPLICATIONS

This application claims the benefit under 35 U.S.C. §119 (e) to U.S. Provisional Patent Application No. 61/425,005, filed on Dec. 20, 2010, entitled "LEAD HAVING A CONDUCTIVE POLYMER CONDUCTOR," which is incorporated herein by reference in its entirety.

TECHNICAL FIELD

The present disclosure generally relates to medical electrical leads and their construction. More particularly, the present disclosure relates to medical electrical leads including one or more conductive polymer conductors.

BACKGROUND

Various types of medical electrical leads for use in cardiac rhythm management (CRM) and neurostimulation applications are known. In CRM applications, for example, such leads are frequently delivered intravascularly to an implantation location on or within a patient's heart. Once implanted, the lead is coupled to a pulse generator or other implantable device for sensing cardiac electrical activity, delivering therapeutic stimuli, and/or for performing some other desired function within the body. Accordingly, there are ongoing efforts to identify lead body materials and lead body constructions that provide the flexibility and minimized profiles that enable the lead to be navigated through the tortuous pathways of a patient's vasculature system, and that can sufficiently withstand exposure to the body environment.

SUMMARY

Example 1 is a medical electrical lead including: a lead body extending from a terminal connector located at a proximal end portion of the lead body to a distal end portion, the lead body comprising at least one outer layer of an insulating material; at least one conductive polymer conductor extending within the lead body from the terminal connector located at the proximal end portion of the lead body in a direction toward the distal end portion of the lead body, the conductive polymer conductor comprising a conductive material incorporated into a polyisobutylene urethane, urea or urethane/urea copolymer; and at least one electrode located on the lead body, the at least one electrode operatively coupled to the at least one conductive polymer conductor extending within the lead body.

Example 2, the medical electrical lead according to Example 1, wherein the conductive polymer conductor further comprises an elongated conductive element encompassed within the polyisobutylene urethane, urea or urethane/urea copolymer.

Example 3, the medical electrical lead according to any one of Examples 1 or 2, wherein the at least one electrode is a defibrillation coil, a ring electrode, or a tip electrode.

Example 4, the medical electrical lead according to any one of Examples 1-3, wherein the terminal connector comprises at least one electrical interconnect in electrical communication with the at least one conductive polymer conductor.

Example 5, the medical electrical lead according to any one of Examples 1-4, wherein the conductive material comprises gold, nickel, silver, platinum, iridium oxide, or combinations thereof.

Example 6, the medical electrical lead according to any one of Examples 1-5, wherein the conductive material comprises graphite, graphene, or combinations thereof.

Example 7, the medical electrical lead according to any one of Examples 1-6, wherein the conductive material comprises graphite nanotubes, carbon nanotubes, or combinations thereof.

Example 8, the medical electrical lead according to any one of Examples 1-7, wherein the conductive material comprises any one of microspheres, nanospheres, filaments, tubes, nanotubes, fibers, or combinations thereof.

Example 9, the medical electrical lead according to any one of Examples 1-8, wherein an amount of the conductive material incorporated into the polyisobutylene urethane, urea or urethane/urea copolymer ranges from about 80 wt. % to about 99 wt. %.

Example 10, the medical electrical lead according to any one of Examples 1-9, wherein an amount of the conductive material incorporated into the polyisobutylene urethane, urea or urethane/urea copolymer ranges from about 90 wt. % to about 99 wt. %.

Example 11, the medical electrical lead according to any one of Examples 1-10, wherein the polyisobutylene urethane, urea or urethane/urea copolymer comprises fluoropolymer diol soft segments, fluorinated polyether diol soft segments, or fluorinated polysiloxane diol soft segments.

Example 12, the medical electrical lead according to any one of Examples 1-11, wherein the polyisobutylene urethane, urea or urethane/urea copolymer comprises polytetramethylene oxide diol soft segments.

Example 13, the medical electrical lead according to any one of Examples 1-12, wherein the at least one outer layer of insulating material comprises a non-conductive polyisobutylene urethane, urea or urethane/urea copolymer.

Example 14 is a method of manufacturing a medical electrical lead including the steps of: incorporating a conductive material into a polyisobutylene urethane, urea or urethane/urea copolymer to form a conductive polyisobutylene urethane, urea or urethane/urea copolymer; extruding the conductive polyisobutylene urethane, urea or urethane/urea copolymer to form an elongate conductive polymer conductor; and forming at least one layer of an insulating polymeric material over the elongate conductive polymer conductor.

Example 15, the method according to Example 14, wherein an amount of the conductive material incorporated into the polyisobutylene urethane, urea or urethane/urea copolymer ranges from about 80 wt. % to about 99 wt. %.

Example 16, the method according to Example 14 or Example 15, wherein an amount of the conductive material incorporated into the polyisobutylene urethane, urea or urethane/urea copolymer ranges from about 90 wt. % to about 99 wt. %.

Example 17, the method according to any one of Examples 14-16, wherein the conductive polyisobutylene urethane, urea or urethane/urea copolymer is extruded over an elongated conductive element.

Example 18, the method according to any one of Examples 14-17, further comprising coupling a terminal connector to the conductive polymer conductor.

Example 19, the method according to any one of Examples 14-18, further comprising coupling an electrode to the conductive polymer conductor.

Example 20, the method according to any one of Examples 14-19, further comprising extruding at least one layer of a non-conductive polyisobutylene urethane, urea or urethane/urea copolymer over the conductive polymer conductor.

Example 21, the method according to any one of Examples 14-20, wherein the at least one layer of insulating polymeric material is extruded over the conductive polymer conductor.

Example 22, the method according to any one of Examples 14-21, wherein the at least one layer of insulating polymeric material is co-extruded with the conductive polymer conductor.

Example 23, the method according to any one of Examples 14-22, wherein the at least one layer of insulating polymeric material is molded over the conductive polymer conductor.

Example 24 is another method of manufacturing a lead including the steps of: forming a lead body comprising at least one lumen extending from a proximal end to a distal end of the lead body; injecting a conductive polymer material comprising a conductive material incorporated into a polyisobutylene urethane, urea or urethane/urea copolymer into the at least one lumen; and curing the polyisobutylene urethane, urea or urethane/urea copolymer to form a conductive polymer conductor within the lumen.

Example 25 is a conductive polymer including: a conductive material incorporated into a polymer matrix comprising a polyisobutylene urethane, urea or urethane/urea copolymer comprising soft polymer segments and hard polymer segments; wherein the soft polymer segments comprise a polyisobutylene segment and at least one additional polymer segment comprising a residue of a polyether diol, a fluorinated polyether diol, a fluoropolymer diol, a polyester diol, a polyacrylate diol, a polymethacrylate diol, a polysiloxane diol, a fluorinated polysiloxane diol, or a polycarbonate diol; and wherein a weight ratio of soft segments to hard segments in the polyisobutylene urethane, urea or urethane/urea copolymer ranges from 50:50 to 90:10.

Example 26, the conductive polymer according to Example 25, wherein the conductive material comprises gold, nickel, silver, platinum, iridium oxide, or combinations thereof.

Example 27, the conductive polymer according to Example 25 or Example 26, wherein the conductive material comprises graphite, graphene, graphite nanotubes, carbon nanotubes, or combinations thereof.

Example 28, the conductive polymer according to any one of Examples 25-27, wherein the conductive material comprises silver particles.

Example 29, the conductive polymer according to any one of Examples 25-28, wherein the soft segments comprise a polyisobutylene segment and a residue of a fluoropolymer diol, a fluorinated polyether diol, or a fluorinated polysiloxane diol.

Example 30, the conductive polymer according to any one of Examples 25-29, wherein an amount of the conductive material incorporated into the polyisobutylene urethane, urea or urethane/urea copolymer ranges from about 80 wt. % to about 99 wt. %.

Example 31, the conductive polymer according to any one of Examples 25-30, wherein an amount of the conductive material incorporated into the polyisobutylene urethane, urea or urethane/urea copolymer ranges from about 90 wt. % to about 99 wt. %.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIG. 2A is a longitudinal, cross-sectional view of a lead in accordance with an illustrative embodiment;

FIG. 2B is an end, cross-sectional view of a lead in accordance with an illustrative embodiment;

FIG. 4 is a longitudinal, cross-sectional view of a lead in accordance with another illustrative embodiment;

FIG. 5 is a flow chart of a method of manufacturing a lead in accordance with another illustrative embodiment.

Figure 1:
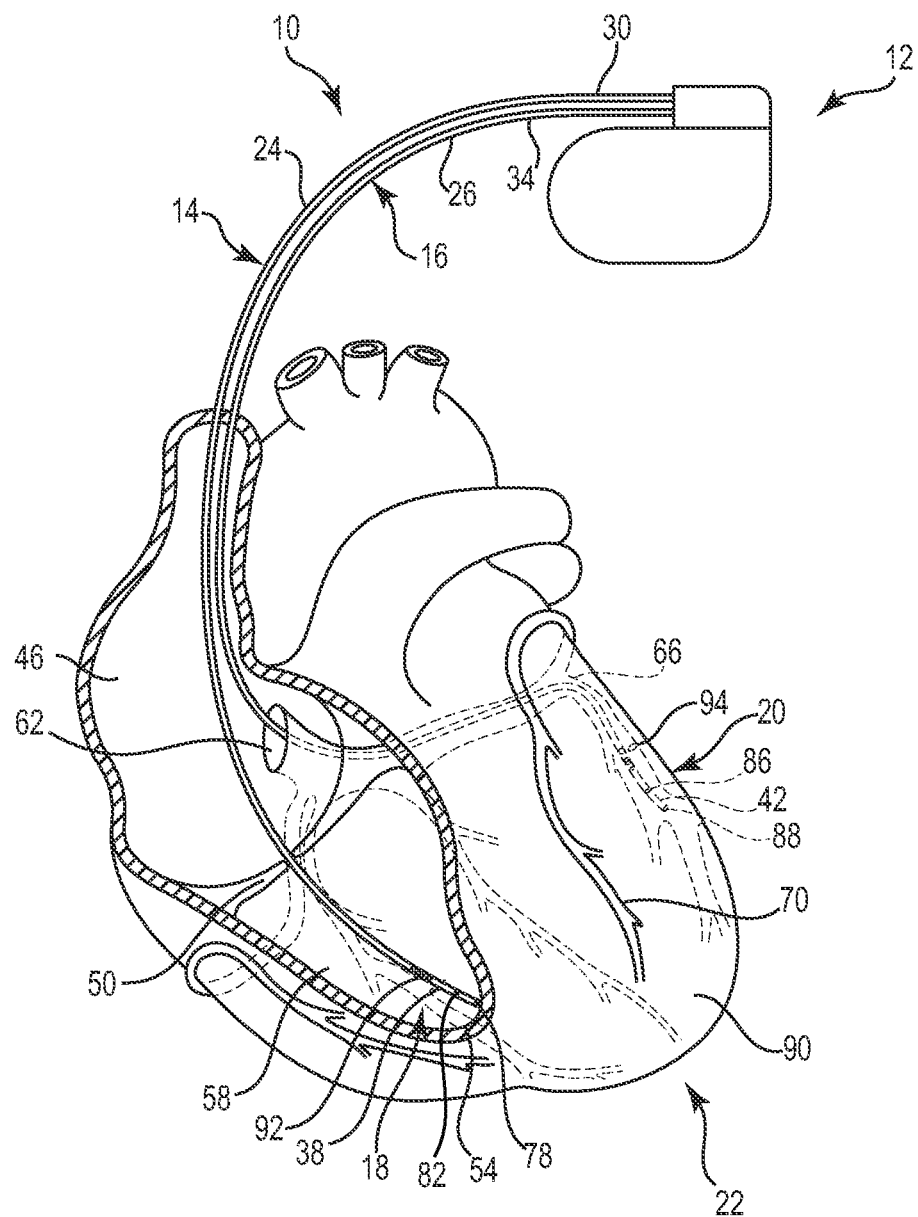
FIG. 1 is a schematic view of an implantable cardiac rhythm management system in accordance with an illustrative embodiment.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

The leads according to the various embodiments described herein are suitable for sensing intrinsic electrical activity and/or applying therapeutic electrical stimuli to a patient. Exemplary applications include, without limitation, cardiac rhythm management (CRM) systems and neurostimulation systems. For example, in exemplary CRM systems utilizing pacemakers, implantable cardiac defibrillators, and/or cardiac resynchronization therapy (CRT) devices, the medical electrical leads according to the various embodiments of the disclosure can be endocardial leads configured to be partially implanted within one or more chambers of the heart so as to sense electrical activity of the heart and apply a therapeutic electrical stimulus to the cardiac tissue within the heart. Additionally, the leads formed according to the various embodiments of the present disclosure may be suitable for placement in a coronary vein adjacent to the left side of the heart so as to facilitate bi-ventricular pacing in a CRT or CRT-D system. Still additionally, leads formed according to embodiments of the present disclosure may be configured to be delivered intravascularly to deliver an electrical stimulation therapy to a nerve or other neurostimulation target. The medical electrical leads may be unipolar, bipolar, or multi-polar depending upon the type of therapy to be delivered.

FIG. 1 is a schematic view of a cardiac rhythm management system 10 that can be used for delivering cardiac pacing therapy in accordance with an illustrative embodiment. The system 10 includes a pulse generator 12 coupled to a number of leads 14, 16 that can be inserted at target implantation pacing sites 18, 20 in or near a patient's heart 22.

Each of the leads 14, 16 include a flexible, lead body 24, 26 extending from a terminal connector (not shown) located at a proximal end portion 30, 34 of each of the lead bodies 24, 26 toward a distal end portion 38, 42. The lead bodies 24, 26 can have a variety of cross-sectional shapes. In one embodiment, the lead bodies 24, 26 have a circular cross-sectional shape. Additionally, the lead bodies 24, 26 can include at least one lumen extending from the proximal end portion 30, 34 to a distal end portion 38, 42. The lumen can facilitate passage of a guiding element such as a guidewire or a stylet for delivery of the leads 14, 16 to implant the leads 14, 16 within the patient's heart 22.

As shown in FIG. 1, the distal end portion 38 of the lead 14 may be transvenously guided through the right atrium 46, through the tricuspid valve 50, and into the apex 54 of the right ventricle 58. The distal end portion 42 of the lead 16, in turn, may be tranvenously guided through the right atrium 46, through the coronary sinus ostium 62, and into a branch vessel of the coronary sinus 66, great cardiac vein 70, or other cardiac vessel located adjacent to the left side of the heart 22.

Each of the leads 14, 16 can include one or more cardiac pace/sense electrodes for sensing electrical measurements within the patient's heart 22 and for delivering pacing pulses and/or defibrillation energy to the heart 22. In some embodiments, for example, the lead 14 includes a number of pacing electrodes 78, 82 for sensing electrical activity within the right ventricle 58 of the heart 22 and/or to provide pacing pulses to the right ventricle 58. The lead 16, positioned in a cardiac vein adjacent to the left side of the heart 22, includes a number of pacing electrodes 86, 88 for sensing electrical activity within the heart 22 and/or to provide pacing pulses to the left ventricle 90. In some embodiments, a number of defibrillation electrode coils 92, 94 provided on one or both of the leads 14, 16 can be utilized to deliver defibrillation/cardioversion shocks to the patient's heart 22, if necessary.

According to various embodiments, the leads 14, 16 can include one or more fixation members for securing and stabilizing the leads 14, 16 including electrodes 78, 82, 86, 88, 92, and/or 94 at a target site within a patient's body. The fixation member(s) can be active or passive. Examples of passive fixation include pre-formed distal portions of the lead body such as, for example, a spiral, adapted to bear against the vessel walls and/or expandable tines provided at the distal end of the lead body. In some embodiments, the fixation member can be a screw-in fixation member. In other embodiments, the fixation member can be an extendable/retractable fixation member and can include one or more mechanical components adapted to facilitate the extension/retraction of the fixation member. An exemplary extendable/retractable fixation member is shown and described in U.S. Pat. No. 6,444,334, which is incorporated herein by reference in its entirety for all purposes.

FIG. 2A is a longitudinal, cross-sectional view and FIG. 2B is an end, cross-sectional view of a lead 100 in accordance with an illustrative embodiment. As shown in FIG. 2A, the lead 100 includes a lead body 104 extending from a proximal end portion 108 in a direction toward a distal end portion 112. A terminal connector 116 adapted to couple the lead 100 to a pulse generator is located at the proximal end portion 108 of the lead body 104. In the illustrated embodiment shown in FIG. 2A, the lead 100 also includes two electrodes 120, 124 located in a distal end portion 112 of the lead body 104. As shown in FIG. 2A, the electrode 120 is a ring electrode 120 and the electrode 124 is a tip electrode 124. It will be generally understood by those of skill in the art that a variety of electrode configurations and combinations of electrode configurations may be employed.

According to various embodiments, the lead 100 includes at least one conductive polymer conductor extending within the lead body 104. In the illustrative embodiment shown in FIGS. 2A and 2B, the lead 100 includes two conductive polymer conductors 128, 132 extending within the lead body 104 from the terminal connector 116 in a direction toward the distal end portion 112. The conductive polymer conductors 128, 132 have sufficient electrical conductivity to carry an electrical current transmitted by a pulse generator (not shown) from the terminal connector 116 to the electrodes 120, 124 located in the distal end portion 112 of the lead body 104.

The conductive polymer conductors 128, 132 can be formed from a variety of conductive polymers. The conductive polymer conductors 128, 132 can be fabricated from an intrinsically conductive polymer or a conductor-filled polymer. Non-limiting examples of intrinsically conductive polymers include poly(pyrrole)s, poly(acetylene)s, polyanilines, poly(thiophene)s, and poly(3-alkylthiophene)s. Non-limiting examples of conductor-filled polymers include polyurethanes, silicone elastomers, or other polymeric materials that are compounded with a conductive material.

In one embodiment, the conductive polymer is a conductor-filled polyisobutylene based polyurethane copolymer such as a polyisobutylene urethane, urea or urethane/urea copolymer. Polyisobutylene urethane, urea or urethane/urea copolymers suitable for use with the various embodiments of the present disclosure, as described herein, are shown and described in U.S. patent application Ser. No. 12/874,887 entitled "Medical Devices Including Polyisobutylene Based Polymers and Derivatives Thereof," which is incorporated herein by reference in its entirety for all purposes.

The polyisobutylene urethane, urea or urethane/urea copolymer includes both hard and soft segments. The weight ratio of hard segments to soft segments in the polyisobutylene urethane, urea or urethane/urea copolymer can range from about 50:50 to about 90:10. The soft segments include a polyisobutylene segment and one additional polymer segment. In certain embodiments, the soft segments can include a polyisobutylene segment and a fluoropolymer diol soft segment, a fluorinated polyether diol soft segment, or a fluorinated polysiloxane diol soft segment. The presence of a fluoro-containing soft segment may enhance some of the conductive properties of the copolymer, and may enhance some of the physical properties of the copolymer such as thermal stability and chemical resistance. Additionally, the presence of a fluoro-containing soft segment may facilitate bonding between the polyisobutylene urethane, urea or urethane/urea copolymer and another polymer.

In another embodiment, the soft segment can include a polyisobutylene segment and a polytetramethylene oxide diol segment. The ratio of polyisobutylene to polytetramethylene oxide diol in the soft segment can range from about 70:30 to about 90:10.

Suitable conductive materials that can be blended with a polyisobutylene urethane, urea or urethane/urea copolymer, as described herein, to form the conductive polymer conductors 128, 132 include, but are not limited to, the following: carbon, graphite, graphene, nickel, silver, gold, platinum, iridium oxide, and combinations thereof. The conductive material can be provided in the form of microparticles or nanoparticles, microfibers or nanofibers, filaments, microspheres or nanospheres, and/or nanotubes. In one embodiment, the conductive material includes graphite nanotubes. In another embodiment, the conductive material includes graphene. In still another embodiment, the conductive material includes silver particles. In still yet another embodiment, the conductive material includes a combination of silver and nickel spheres.

To form the conductive polymer conductor, the conductive material is blended with a polyisobutylene urethane, urea or urethane/urea copolymer in an amount sufficient to provide the electrical conductivity needed to transmit an electrical current from the terminal connector 116 located at the proximal end portion 108 of the lead body 104 to the electrodes 120, 124 located at a distal end portion 112 of the lead body 104. Additionally, the conductive material should be incorporated into the copolymer in an amount such that it does not negatively impact the other beneficial physical properties of the polyisobutylene urethane, urea or urethane/urea copolymer.

In one embodiment, the amount of conductive material blended with the polyisobutylene urethane, urea or urethane/urea copolymer to form a conductive polymer conductor ranges from about 5 wt. % to about 99 wt. % (weight of the conductive material/total weight of the copolymer and the conductive material). In one embodiment, the amount of conductive material ranges from about 80 wt. % to about 99 wt. % and more particularly, from about 90 wt. % to about 99 wt. %. In other embodiments, the amount of conductive material incorporated into the copolymer ranges from about: 5 wt. % to about 85 wt. %; from about 5 wt. % to about 75 wt. %; from about 5 wt. % to about 65 wt. %; from about 5 wt. % to about 50 wt. %; from about 5 wt. % to about 40 wt. %; from about 5 wt. % to about 30 wt. %; from about 5 wt. % to about 25 wt. %; from about 5 wt. % to about 15 wt. %; and more particularly, from about 5 wt. % to about 10 wt. %.

As shown in FIGS. 2A and 2B, the lead 100 also includes at least one layer of an insulating polymeric material 136. The layer of insulating polymeric material 136 is disposed over and surrounds each of the conductive polymer conductors 128, 132, and, in some embodiments, the layer 136 is an outer layer of insulation that forms an outer surface 138 of the lead body 104. At least one additional layer 140 of insulating material electrically insulates the first polymer conductor 128 from the second polymer conductor 132.

The insulating polymeric material used to form the lead body 104 can include a variety of different biocompatible polymeric materials, polymeric material blends, co-block polymers, copolymers, and elastomers used to manufacture lead bodies known to those of skill in the art. In certain embodiments, at least one layer of insulation is formed from a non-conductive polyisobutylene based polyurethane copolymer such as a polyisobutylene urethane, urea or urethane/urea copolymer as described herein. The layer of polyisobutylene urethane, urea or urethane/urea copolymer can be used as an outer layer 136 and/or an inner layer 140 of insulation.

Figure 3A:
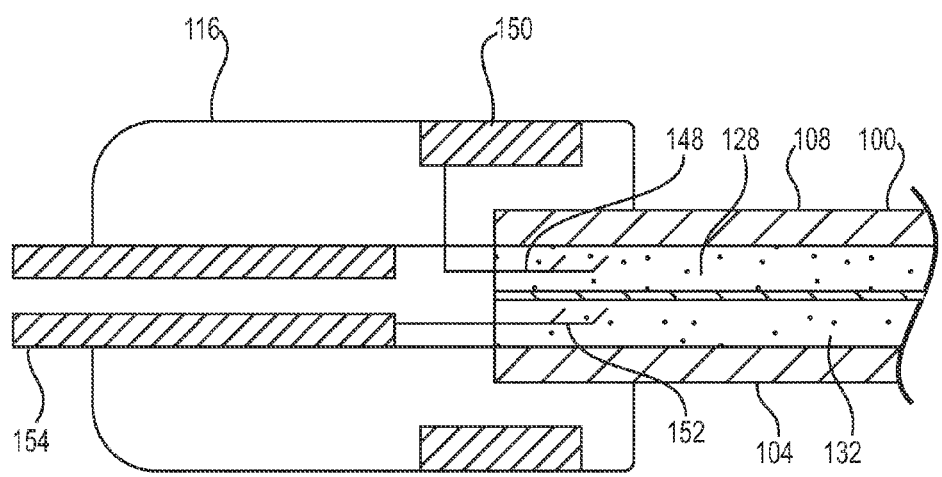
FIGS. 3A and 3B are close-up, schematic views of different portions of the lead shown in FIG. 2A.
Figure 3B:
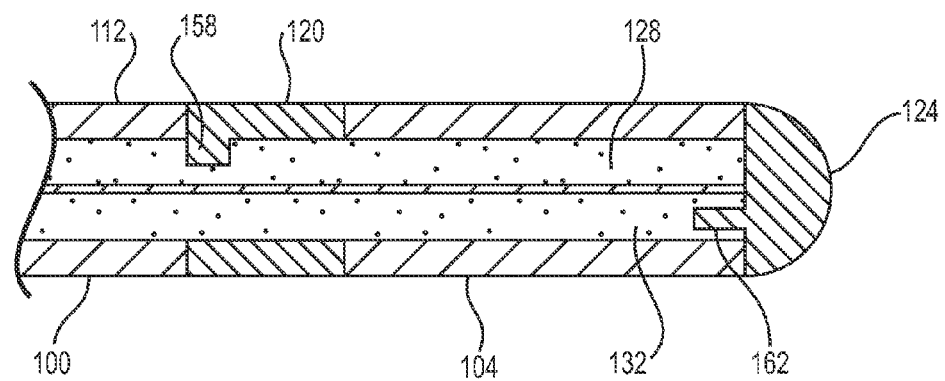

FIGS. 3A and 3B are close-up views of the proximal end portion 108 and the distal end portion 112, respectively, of the lead 100 illustrating the electrical connection between the terminal connector 116, the electrodes 120, 124, and the conductive polymer conductors 128, 132. In one embodiment, the terminal connector 116 includes at least one electrical interconnect electrically coupling the terminal connector 116 to the conductive polymer conductors 128, 132 extending within the lead body 104. In the illustrated embodiment, the terminal connector 116 includes a first electrical interconnect 148 electrically coupling the ring electrode 150 to the first conductive polymer conductor 128 and a second electrical interconnect 152 electrically coupling the terminal pin 154 to the second conductive polymer conductor 132. Each of the electrical interconnects 148, 152 can be a wire, pin, or post that extends from the ring electrode 150 and/or the terminal pin 154 into the conductive polymer conductor 128, 132, respectively. As shown in FIG. 3B, the electrodes 120, 124 also include electrical interconnects 158, 162 extending from the electrodes 120, 124 into the conductive polymer conductors 128, 132, electrically coupling the electrodes 120, 124 to the conductive polymer conductors 128, 132.

The electrical interconnects 148, 152, 158, 162 can be electrically coupled with the conductive polymer conductors 128, 132 using a variety of bonding techniques. In one embodiment, the electrical interconnects 148, 152, 158, 162 are inserted into the conductive polymer conductors 128, 132 prior to curing of the conductive polymer conductors 128, 132. In other embodiments, the electrical interconnects 148, 152, 158, 162 are coupled to the conductive polymer conductors 128, 132 through the application of heat or an adhesive such as a conductive adhesive. Additionally, the electrical interconnects 148, 152, 158, 162 can include barbs or other surface area enhancing features to increase the contact area between the electrical interconnects 148, 152, 158, 162 and the conductive polymer conductors 128, 132.

FIG. 4 is a longitudinal, cross-sectional view of a lead 200 in accordance within another embodiment. In the illustrative embodiment shown in FIG. 4, the lead 200 includes a lead body 204 including a proximal end portion 208 and a distal end portion 212. A terminal connector 216 adapted to couple the lead 200 to a pulse generator is located at the proximal end portion 208 of the lead body 204. The lead 200 also includes a coil electrode 220 and a tip electrode 224 located in a distal end portion 212 of the lead body 204. Two conductive polymer conductors 228, 232 extend within the lead body 204 from the terminal connector 216 in a direction toward the distal end portion 212. In certain embodiments, the conductive polymer conductors 228, 232 are fabricated from a conductor-filled polyisobutylene urethane, urea or urethane/urea copolymer as described herein according to the various embodiments of the present disclosure.

For higher voltage applications such as, for example, defibrillation, at least one of the conductive polymer conductors 228 or 232 can be disposed over a thin, elongated conductive element 244, as shown in FIG. 4. The elongated conductive element 244 can be any one of a wire, a braided wire, a helical hollow strand, a hollow core wire, or a drawn filled tube. The elongated conductive element 244 extending within the conductive polymer conductor 228 provides an electrically conductive backbone, and may increase the mechanical properties of the conductive polymer conductor 228. The elongated conductive element 244 may also provide additional connection points for additional electrodes located on the lead body 204.

FIG. 5 is a flow chart outlining one method 300 of manufacturing a lead as described herein according to the various embodiments. First, conductive particles are blended with a polyisobutylene urethane, urea or urethane/urea copolymer to form a conductive polyisobutylene urethane, urea or urethane/urea copolymer (Block 310). The conductive particles can be blended with the polyisobutylene urethane, urea or urethane/urea copolymer using a static mixer. The conductive particles are blended with the polyisobutylene urethane, urea or urethane/urea copolymer in an amount sufficient to conduct an electrical current along a length of the lead body from a terminal connector to an electrode located in a distal end portion of the lead body. In one embodiment, the amount of conductive particles blended with the polyisobutylene urethane, urea or urethane/urea copolymer ranges from about 80 wt. % to about 99 wt. % and more particularly, from about 90 wt. % to about 99 wt. %.

The conductive polyisobutylene urethane, urea or urethane/urea copolymer is then extruded to form at least one elongated conductive polymer conductor (Block 320). In one embodiment, the conductive polyisobutylene urethane, urea or urethane/urea copolymer is extruded over an elongate conductive member. Next, at least one layer of an insulating polymeric material is extruded over the elongated conductive polymer conductor to form a lead body (Block 330). Additional layers of insulation may be applied. In other embodiments, the conductive polymer conductor and the insulating polymeric material can be co-extruded to form the lead body. In one embodiment, at least one layer of insulation is formed from a polyisobutylene urethane, urea or urethane/urea copolymer as described herein.

A terminal connector and one or more electrodes may be attached to the conductive polymer conductor via one or more electrical interconnects as described herein. The terminal connector and/or electrode(s) can be attached to the conductive polymer conductor using an over-molding or an injection molding process in which the conductive polymer conductor is molded over the one or more electrical interconnects extending from the terminal connector and/or electrode(s). In another embodiment, the terminal connector and the one or more electrical interconnects can be attached to the conductive polymer conductor prior to curing of the conductive polymer.

Figure 6:
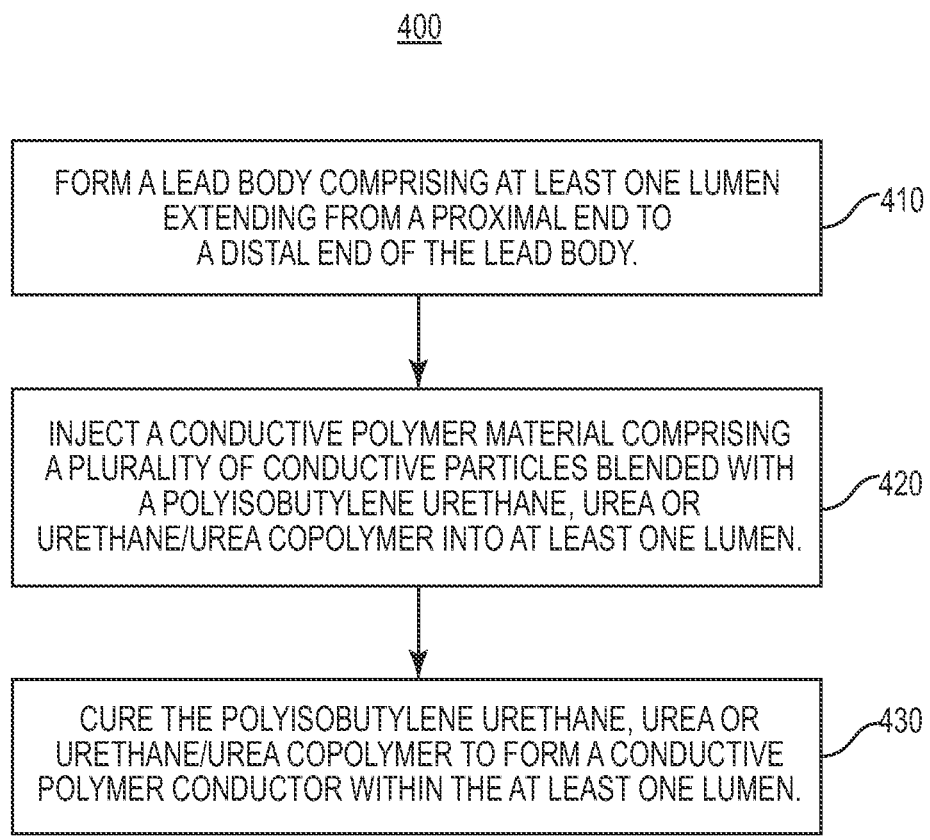
FIG. 6 is a flow chart of a method of manufacturing a lead in accordance with yet another illustrative embodiment.

FIG. 6 is a flow chart outlining another method 400 that can be used to manufacture a lead as described herein according to the various embodiments. First, a lead body is formed from an insulating polymeric material (Block 410). The lead body includes at least one lumen extending from a proximal end toward a distal end of the lead body. The lead body can include one or more layers of an insulating polymeric material. In one embodiment, at least one layer is formed from a polyisobutylene urethane, urea or urethane/urea copolymer as described herein.

Next, a conductive polymer material is injected into the at least one lumen to form a conductive polymer conductor (Block 420). A vacuum may be applied to one end of the lumen during the injection process to eliminate voids in the conductive polymer material and to minimize or eliminate the formation of any air bubbles. In one embodiment, the conductive polymer material includes a plurality of conductive particles blended with a polyisobutylene urethane, urea or urethane/urea copolymer. The conductive particles are blended with the polyisobutylene urethane, urea or urethane/urea copolymer in an amount sufficient to conduct an electrical current along a length of the lead body from a terminal connector to an electrode located in a distal end portion of the lead body. In one embodiment, the amount of conductive particles blended with the polyisobutylene urethane, urea or urethane/urea copolymer ranges from about 80 wt. % to about 99 wt. % and more particularly, from about 90 wt. % to about 99 wt. %. The conductive polyisobutylene urethane, urea or urethane/urea copolymer is then cured to form a conductive polymer conductor extending within the at least one lumen (Block 430).

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A medical electrical lead comprising:
   a lead body extending from a terminal connector located at a proximal end portion of the lead body to a distal end portion, the lead body comprising at least one outer layer of an insulating material, the insulating material including a polyisobutylene urethane, urea or urethane/urea copolymer;
   at least one conductive polymer conductor extending within the lead body from the terminal connector located at the proximal end portion of the lead body in a direction toward the distal end portion of the lead body, the conductive polymer conductor comprising a conductive material blended within a polyisobutylene urethane, urea or urethane/urea copolymer; and
   at least one electrode located on the lead body, the at least one electrode operatively coupled to the at least one conductive polymer conductor extending within the lead body.

2. The medical electrical lead according to claim 1, wherein the at least one conductive polymer conductor further comprises an elongated conductive element encompassed within the polyisobutylene urethane, urea or urethane/urea copolymer.

3. The medical electrical lead according to claim 1, wherein the at least one electrode is a defibrillation coil, a ring electrode, or a tip electrode.

4. The medical electrical lead according to claim 1, wherein the conductive material comprises gold, nickel, silver, platinum, iridium oxide, or combinations thereof.

5. The medical electrical lead according to claim 1, wherein the conductive material comprises graphite, graphene, or combinations thereof.

6. The medical electrical lead according to claim 1, wherein the conductive material comprises graphite nanotubes, carbon nanotubes, or combinations thereof.

7. The medical electrical lead according to claim 1, wherein the conductive material comprises any one of microparticles, nanoparticles, microspheres, nanospheres, filaments, tubes, nanotubes, fibers, or combinations thereof.

8. The medical electrical lead according to claim 1, wherein an amount of the conductive material incorporated into the polyisobutylene urethane, urea or urethane/urea copolymer ranges from about 80 wt. % to about 99 wt. %.

9. The medical electrical lead according to claim 1, wherein an amount of the conductive material incorporated into the polyisobutylene urethane, urea or urethane/urea copolymer ranges from about 90 wt. % to about 99 wt. %.

10. The medical electrical lead according to claim 1, wherein the polyisobutylene urethane, urea or urethane/urea copolymer comprises fluoropolymer diol soft segments, fluorinated polyether diol soft segments, or fluorinated polysiloxane diol soft segments.

* * * * *